United States Patent
Ning

(10) Patent No.: US 8,543,196 B2
(45) Date of Patent: *Sep. 24, 2013

(54) LIE DETECTION BASED ON HEART RATE VARIABILITY

(75) Inventor: Xinbao Ning, Nanjing (CN)

(73) Assignee: Nanjing University, Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,456

(22) Filed: Feb. 28, 2012

(65) Prior Publication Data

US 2012/0157869 A1    Jun. 21, 2012

Related U.S. Application Data

(63) Continuation of application No. 12/466,759, filed on May 15, 2009, now Pat. No. 8,155,733.

(51) Int. Cl.
*A61B 5/0468* (2006.01)

(52) U.S. Cl.
USPC .......................................... 600/509; 128/925

(58) Field of Classification Search
USPC .................... 600/483, 508, 509; 128/925
See application file for complete search history.

(56) References Cited

U.S. PATENT DOCUMENTS

| | | |
|---|---|---|
| 2004/0019289 A1 | 1/2004 | Ross |
| 2005/0256414 A1 | 11/2005 | Kettunen et al. |
| 2008/0177157 A1 | 7/2008 | Pasricha et al. |

FOREIGN PATENT DOCUMENTS

| | | |
|---|---|---|
| CN | 101642368 A | 2/2010 |
| CN | 101642369 A | 2/2010 |

OTHER PUBLICATIONS

Zhuang Jian-Jun, et al "Agreement of two entropy-based measures on quantifying the complexity of short-term heart rate variability signals from professional shooters" Acta Physica Sinica, vol. 57, No. 5, May 2008 pp. 2805-2811.

Qu Jianshi, et al "Recommendation of guideline for heart rate variability measurement and analysis" Chin J Cardiac Arrhyth 1997, vol. 1 No. 2 pp. 135-140.

Li Jin, et al "The base-scale entropy analysis of short-term heart rate variability signal" Chinese Science Bulletin 2005, vol. 50 No. 12 pp. 1269-1273.

Zhuang Jian-Jun, et al "Nonlinear short-term heart rate variability prediction of spontaneous ventricular tachyarrhythmia" Chinese Science Bulletin, Aug. 2008, vol. 53, No. 16, pp. 2446-2453.

Ning Xinbao, et al "Research progress in nonlinear analysis of heart electric activities" Chinese Science Bulletin 2006, vol. 51, No. 4 pp. 385-393.

Zhenzhou Wang, et al "Nonlinear Dynamic Characteristics Analysis of Synchronous 12-Lead ECG Signals—Providing New Insight and Methods in the Diagnosis of Cardiac Disease" IEEE Engineering in Medicine and Biology, Sep./Oct. 2000 pp. 110-115.

Li Jin, et al "Nonlinear Dynamical Complexity Analysis of Short-term Heartbeat Series Using Joint Entropy" J Biomed Eng 2007, vol. 24, No. 2 pp. 285-289.

(Continued)

*Primary Examiner* — Carl H Layno
*Assistant Examiner* — Eugene Wu
(74) *Attorney, Agent, or Firm* — Maschoff Brennan

(57) ABSTRACT

The present disclosure provides computer readable storage media useful in lie detection based on heart rate variability (HRV) analysis and HRV analysis using strange entropy. The computer readable storage medium may have a computer program encoded thereon, the computer program, when executed by a computer, instructs the computer to execute a method of lie detection that includes receiving an input associated with HRV and performing a nonlinear HRV analysis based on the input associated with HRV to obtain a lie detection result, the nonlinear HRV analysis.

17 Claims, 12 Drawing Sheets

(56) References Cited

OTHER PUBLICATIONS

Yang Xi, et al "Clinical application and research based on the analysis of short-term physiological series with base scale entropy" Journal of Nanjing University (Natural Sciences) vol. 44 No. 4, Jul. 2008 pp. 361-370.

Qian Zhong, et al "On the Measuring Instrument for the Heart Rate Variability" Journal of Nanjing University (Natural Sciences) vol. 35, No. 1, Jan. 1999 pp. 89-94.

Xinbao Ning, et al "Approximate entropy analysis of short-term HFECG based on wave mode" Physica A vol. 346, 2005, pp. 475-483.

Jian Jun Zhuang, et al "Alteration in scaling behavior of short-term heartbeat time series for professional shooting athletes from rest to exercise" Physica A vol. 387, Issue 26, Nov. 15, 2008, pp. 6553-6557.

Jin Li, et al "Dynamical complexity detection in short-term physiological series using base-scale entropy" Physical Review E vol. 73, 2006, pp. 052902-1-052902-4.

Jun Wang, et al "Multiscale multifractality analysis of a 12-lead electrocardiogram" Physical Review E vol. 71, 2005, pp. 062902-1-062902-4.

United States Notice of Allowance dated Nov. 30, 2011 in U.S. Appl. No. 12/466,759.

United States Office Action dated Aug. 15, 2011 in U.S. Appl. No. 12/466,759.

United States Office Action dated Mar. 24, 2011 in U.S. Appl. No. 12/466,759.

LIE DETECTION BASED ON HEART RATE VARIABILITY

CROSS-REFERENCE TO RELATED APPLICATION

This patent application is a continuation of U.S. patent application Ser. No. 12/466,759, filed May 15, 2009 now U.S. Pat. No. 8,155,733, which is incorporated herein by reference.

TECHNICAL FIELD

The present disclosure is in the general field of life science, and more particularly bioinformatics.

BACKGROUND

Heart rate variability (HRV) is a measure of the beat-to-beat variations in heart beat and it may be regarded as an indicator of the activity of autonomic regulation of circulatory function in response to an external or internal stimulation.

An analysis of HRV may find use in lie detection, which is generally performed based on body reactions not easily controlled by conscious mind, including, but not limited to, heart rate and skin conductivity. While the subject is asked a series of questions, lying will typically produce distinctive measurements of physiological responses of autonomic nervous system, due to emotional and psychological changes of the subject during questioning.

SUMMARY

Technologies described herein generally include computer readable storage media having a computer program encoded thereon, wherein said computer program when executed by a computer instructs the computer to execute a method of lie detection as described in the present disclosure.

Technologies described herein generally include computer readable storage media having a computer program encoded thereon, wherein said computer program when executed by a computer instructs the computer to perform HRV analysis using strange entropy as described in the present disclosure.

The foregoing is a summary and thus contains, simplifications, generalizations, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
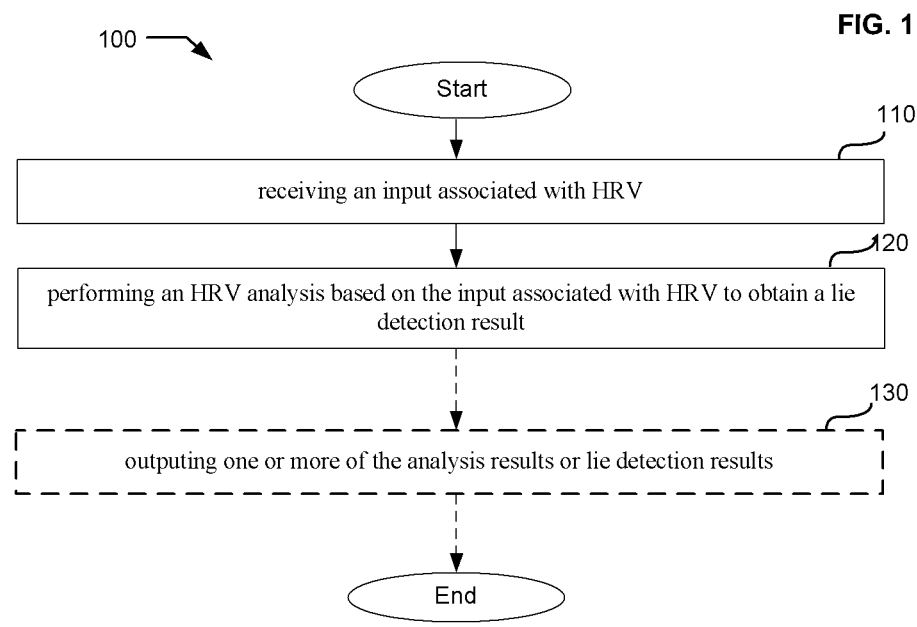
FIG. 1 is a flow chart showing an illustrative embodiment of a lie detection method described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure provides, inter alia, methods, computer program products, computer readable storage media and systems for lie detection based on HRV analysis and for HRV analysis using strange entropy.

In one aspect, the present disclosure provides a method of lie detection, which comprises receiving an input associated with HRV; and performing an HRV analysis based on the input associated with HRV to obtain a lie detection result, wherein said HRV analysis includes one or more of nonlinear HRV analysis, or neural network-based linear HRV analysis.

FIG. 1 shows an operational flow 100 representing an illustrative embodiment of the lie detection method provided in the present disclosure. As shown in FIG. 1, the methods include an input receiving operation 110, that includes receiving an input associated with HRV; an analysis operation 120, that includes performing an HRV analysis based on the input associated with HRV to obtain a lie detection result; and an optional output operation 130, that includes outputting one or more of the analysis results or lie detection results.

In FIG. 1 and in the following figures that include various illustrative embodiments of operational flows, discussion and explanation may be provided with respect to methods and apparatus described herein, and/or with respect to other examples and contexts. The operational flows may also be executed in a variety of other contexts and environments, and/or in modified versions of those described herein. In addition, although some of the operational flows are presented in sequence, the various operations may be performed in various repetitions, concurrently, and/or in other orders than those that are illustrated.

In the input receiving operation 110, an input associated with HRV is received. The input associated with HRV useful for lie detection as described herein may be any measurements that are able to indicate and/or calculate HRV, including, without limitation, measurements derived from ECG, arterial pressure tracking, and pulse wave signal measured by means of e.g. photoplethysmograph (PPG). In an illustrative embodiment, the input associated with HRV includes a time series of ECG recordings.

In some embodiments, the input associated with HRV is received at the same site as where the analysis operation is executed. In other embodiments, the input associated with HRV may be obtained remotely from a site where the analysis operation is executed. In illustrative embodiments, the input associated with HRV of a subject is received and then analyzed in a different place from where questioning and measurements take place. These measurements can be transmitted to the site of analysis by any suitable wireless/wired communication methods, including, without limitation, GSM/GPRS network, Bluetooth, internet and any equivalent means.

In some embodiments, the input associated with HRV is received in a real-time manner. In other embodiments, the measurements may be stored in a database and retrieved later to generate the input.

From the input receiving operation 110, the operational flow 100 moves to the analysis operation 120, where a HRV analysis is performed based on the input associated with HRV to obtain a lie detection result. Said HRV analysis includes one or more of nonlinear HRV analysis, or neural network based-linear HRV analysis. In an illustrative embodiment, said HRV analysis includes nonlinear HRV analysis. In another illustrative embodiment, said HRV analysis includes neural network-based linear HRV analysis. In yet another illustrative embodiment, said HRV analysis includes neural network-based linear HRV analysis in combination with nonlinear HRV analysis, and the neural network analysis is performed based on a combination of linear HRV parameters and nonlinear HRV parameters.

Various nonlinear analysis methods may be adapted to be used in the HRV-based lie detection method provided in the present disclosure. Illustrative examples of useful nonlinear analysis methods include, but are not limited to, strange entropy (StEn), Chaos, correlation dimension, fractal theory, strange attractors, mode entropy (modEn), multifractal, multiscale multifractal, Lyapunov index, base-scale entropy, and approximate entropy (ApEn). In an illustrative embodiment, the nonlinear HRV analysis is performed using strange entropy method as detailed below.

In some embodiments, performing an HRV analysis based on the input associated with HRV using neural network-based linear HRV analysis includes acquiring one or more linear HRV parameters from the input associated with HRV; and performing a neural network analysis based on the linear HRV parameters.

In some embodiments, performing an HRV analysis based on the input associated with HRV using neural network-based linear HRV analysis in combination with nonlinear HRV analysis includes acquiring one or more linear HRV parameters from the input associated with HRV; obtaining one or more nonlinear HRV parameters from the input associated with HRV; and performing a neural network analysis based on the one or more linear HRV parameters and the one or more nonlinear HRV parameters.

Figure 2:
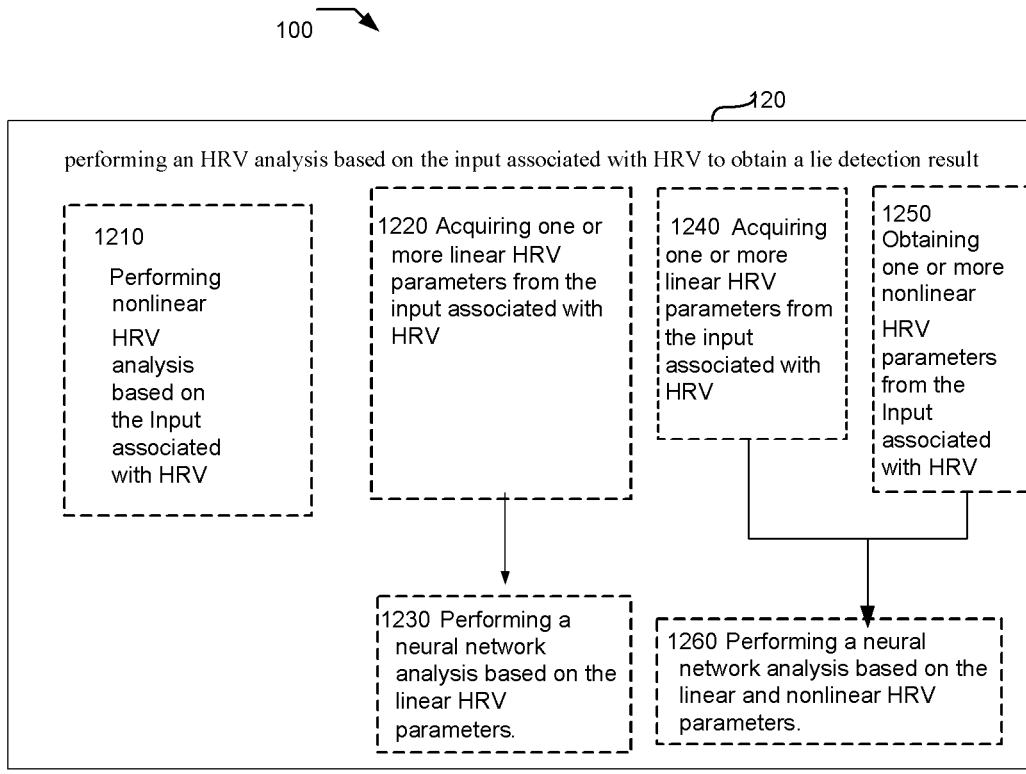
FIG. 2 shows illustrative embodiments of performing an HRV analysis described herein.

FIG. 2 illustrates optional embodiments of the analysis operation 120. The analysis operation 120, performing an HRV analysis based on the input associated with HRV, may optionally include, but are not limited to, operation 1210 representing illustrative embodiments of nonlinear HRV analysis, operations 1220 to 1230 representing illustrative embodiments of neural network-based linear HRV analysis, and operations 1240 to 1260 representing illustrative embodiments of neural network-based linear HRV analysis in combination with nonlinear HRV analysis.

At the optional operation 1210, a nonlinear HRV analysis based on the input associated with HRV may be performed.

In an illustrative embodiment, the nonlinear HRV analysis is performed by using strange entropy method.

In certain embodiments, said strange entropy method may include taking a time series signal with N elements; calculating the base scale BS(i) for each vector X(i); calculating probability of S(i); and obtaining one or more of nonlinear HRV parameters or m-word distribution graph according to the probability of S(i). Accordingly, the present disclosure provides a method of HRV analysis using strange entropy.

In some embodiments, said strange entropy method includes taking a time series signal with N elements, u: {u(i): $1 \leq i \leq N$}, wherein u(i) represents signals carried in the input associated with HRV, and for each u(i), there is a corresponding vector with m elements X(i)=[u(i), u(i+1), ..., u(i+m−1)]; calculating a base scale BS(i) for each vector X(i); transforming every X(i) to a m-dimensional symbol series $S_i$={s(i), ... s(i+m−1)}, s∈A (A=0, 1, 2, 3) based on a scale of a×BS(i); calculating the probability of $S_i$, wherein the probability of each different combination among the entire N−m+1 m-dimensional vectors is $$p(\pi) = \frac{\#\{t \mid (u_i, \ldots, u_{t+m-1}) \text{ has type } \pi\}}{N - m + 1},$$

wherein $1 \leq t \leq N-m+1$; # is the number of states, and each possible combination π for $S_i$ represents a vibration mode for $S_i$; and obtaining one or more of nonlinear HRV parameters or m-word distribution graph according to the probability of $S_i$.

Figure 3:
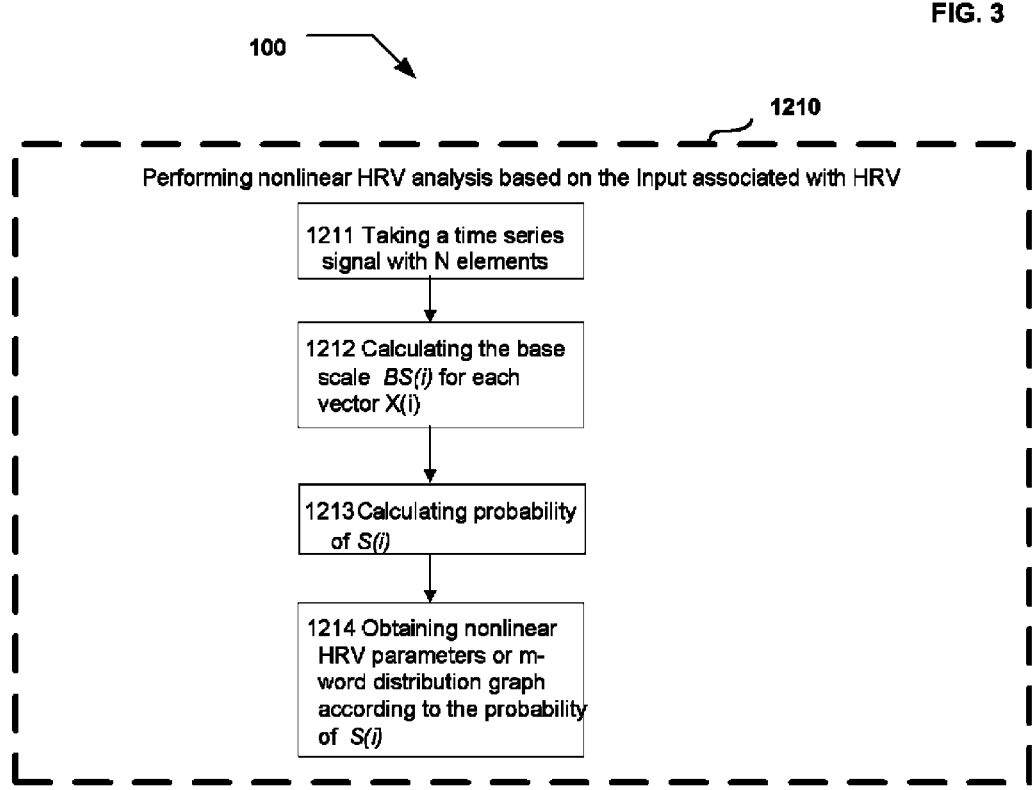
FIG. 3 is a flow chart showing an illustrative embodiment of nonlinear HRV analysis using strange entropy.

FIG. 3 shows an operational flow illustrating this embodiment, including operations 1211 to 1214.

At operation 1211, a time series signal with N elements may be taken, for instance, u: {u(i):$1 \leq i \leq N$}, wherein u(i) represents signals carried in the input associated with HRV. In illustrative embodiments, N needs to be larger than $4^m$. In some embodiments, u(i) represents beat-to-beat interval. In an illustrative embodiment, u(i) represents R-R interval, derived from e.g. ECG recordings. For each u(i), there is a corresponding vector with m elements X(i)=[u(i), u(i+1), ..., u(i+m−1)], wherein m can be in the range of 2-6. In an illustrative embodiment, m is 4.

At operation 1212, the base scale (BS) BS(i) for each vector X(i) may be calculated. BS(i) is defined as the square root average of difference between adjacent elements. In illustrative embodiments, BS(i) is calculated according to the following equation $$BS(i) = \sqrt{\frac{\sum_{j=1}^{m-1}(u(i+j)-u(i+j-1))^2}{m-1}}.$$

Based on a scale of a×BS(i), every X(i) may be transformed to a m-dimensional symbol series $S_i=\{s(i), \ldots s(i+m-1)\}$, s∈A (A=0, 1, 2, 3). In illustrative embodiments, the transformation equation is $$S_{i+k} = \begin{cases} 0: \overline{u}_i < u_{i+k} \leq \overline{u}_i + a \times BS(i) \\ 1: u_{i+k} > \overline{u}_i + a \times BS(i) \\ 2: \overline{u}_i - a \times BS(i) < u_{i+k} \leq \overline{u}_i \\ 3: u_{i+k} \leq \overline{u}_i - a \times BS(i) \end{cases}$$

wherein i=1, 2, . . . , N−m+1; k=0, 1, . . . m−1; $S_{i+k}$ is the k-th element of $S_i$; $u_{i+k}$ is the k-th element of X(i); $\overline{u}_i$ represents the average value of the m-dimensional vector X(i); BS(i) represents the base scale of X(i). 0, 1, 2, 3 are merely illustrative notation for region partition and the value assignments do not stand for any actual meanings. The value assignment of a cannot be too small to ignore noise, or too large, in case that detail information may be lost during the transformation from original time series to symbol series and thus inadequate for capturing the dynamic information in the signal. In illustrative embodiments, a can be in the range of 0.1-2. In certain embodiments, a can be in the range of 0.1-0.4. In an illustrative embodiment, a is 0.2.

At operation 1213, the probability of $S_i$ may be calculated. Accordingly the probability of each different combination among the entire N−m+1 m-dimensional vectors may be calculated. In illustrative embodiments, the probability of $S_i$ may be calculated using the following equation $$p(\pi) = \frac{\#\{t \mid (u_i, \ldots, u_{t+m-1}) \text{ has type } \pi\}}{N-m+1}$$

wherein 1≤t≤N−m+1, # is the number of states, and each possible combination π for $S_i$ represents a vibration mode for $S_i$. The combinations with the probability of $S_i$ equaling to zero are noted as a forbidden state.

At operation 1214, one or more of nonlinear HRV parameters or m-word distribution graph according to the probability of $S_i$ may be obtained. In illustrative embodiments, nonlinear HRV parameters or m-word distribution graph may be obtained by defining the parameter H(m) (strange entropy, StEn) according to the following formula $$H(m) = -\Sigma P(\pi)\log_2 P(\pi).$$

H(m) describes the information of m continuous values in time series. In illustrative embodiments, if there are π states with the same probability, then $H(m)=\log_2 4^m$; if there is only one possible state in time series, then H(m)=0. For situations in between, there is $0<H(m)<\log_2 4^m$. High entropy indicates complexity in time series. On the other hand, low entropy indicates order in series.

Nonlinear HRV parameters or m-word distribution graph according to the probability of $S_i$ can also be obtained by defining the parameter probability of strange states (PSS) used to indicate the sum of probabilities of all strange states, calculated according to the following equation $$PSS = \frac{\sum P_s}{\sum_{i=0}^{255} P_i}$$

wherein $P_i$ is probability of combination i, $P_s$ is probability of strange state, $\Sigma P_s$ is probability sum of all strange states.

PSS reflects the ratio of e.g. four healthy combinations among all possible combinations. A larger PSS value means a more healthy vibration mode.

After acquiring one or more of nonlinear HRV parameters, such as H(m) and PSS, or m-word distribution graph, by nonlinear HRV analysis, using one or more of strange entropy or other methods, a conclusion of whether a person is lying or not may be drawn by interpreting those nonlinear parameters and/or graphs, both independently and in various combinations.

In certain embodiments, the lie detection result is obtained by comparing analysis results obtained from a test subject with normal data. The normal data may include, without limitation, data obtained from the same test subject while he/she is in a normal state without any stimulation or disturbance, and data obtained from normal population in general. Any identifiable difference between the data obtained from the test subject and normal data suggests that the test subject may be under abnormal psychological conditions such as lying. In an illustrative embodiment, the difference is significant.

In certain embodiments, the lie detection result is obtained by real-time monitoring using a sliding window. The test subject may be monitored for one or more of those nonlinear parameters or graphs during a lie detection test in a real-time manner using a sliding window. As a lie detection test usually takes a relatively long time, there will be enough number of data points to be analyzed. In illustrative embodiments, the data points represent heart beats. The sliding window will typically include an appropriate number of data points. In certain embodiments, the window size could be in the range of 300-500 data points with the data points representing heart beats. In this embodiment, the window size is equivalent to the number of data points obtained within around 2-6 minutes given a heart rate of about 80 or more. In illustrative embodiments, the sliding step could be between 1 and 50 data points.

In addition to nonlinear HRV analysis as described above, a lie detection result may also be obtained by performing neural network-based linear HRV analysis. In illustrative embodiments, the analysis operation 120 may include optional operations 1220 to 1230, as shown in FIG. 2.

At the optional operation 1220, one or more linear HRV parameters may be acquired from the input associated with HRV.

The linear HRV parameters, including, without limitation, frequency-domain parameters, such as total power (TP), low frequency (LF) power, high frequency (HF) power, normalized LF (LFnorm), normalized HF (HFnorm), low frequency power/ high frequency power (LF/HF), and time-domain parameters, such as heart rate (HR), and standard deviation of adjacent R-R Interval (rMSSD), may be obtained from linear HRV analysis and are interdependent.

Linear HRV analysis can be carried out in either or both of frequency-domain and time-domain.

Usually time-domain analysis is suitable for long-term analysis, for instance, as long as 24 hours or even longer. In an illustrative embodiment, HR analysis could be performed to monitor slow-changing part in HRV. In another illustrative embodiment, an rMSSD analysis could be performed to monitor fast-changing part in HRV, which can be calculated by using the following equation:

$$rMSSD = \sqrt{\sum_{i=1}^{n-1}(X_{i+1} - X_i)^2/(n-1)} \text{ (ms)},$$

wherein X stands for beat-to-beat interval, e.g. R-R interval.

Frequency-domain analysis is often used for short-term analysis, which may last 5 minutes for instance.

In illustrative embodiments, frequency-domain parameters may be calculated according to the definition of HRV spectrum segment.

In illustrative embodiments, the ultra low frequency (ULF) power indicates a power at a frequency lower than 0.003 Hz, the very low frequency (VLF) power indicates a power at a frequency lower than 0.04 Hz, the low frequency (LF) power indicates a power at a frequency within a range from 0.04 Hz to 0.15 Hz, and the high frequency (HF) indicates a power at a frequency within a range from 0.15 Hz to 0.4 Hz. The calculation of the total power (TP) is to calculate a sum of powers of all frequency domain data corresponding to the heart rate data within a certain frequency range, e.g. a range under 0.4 Hz. In other words, the TP is obtained by adding the powers of all the frequency domain data corresponding to the heart rate data. The calculation of the LF power is to calculate a sum of powers of all frequency domain data corresponding to the heart rate data within a range from 0.04 Hz to 0.15 Hz. The calculation of the HF power is to calculate a sum of powers of all frequency domain data corresponding to the heart rate data within a range from 0.15 Hz to 0.4 Hz. The calculation of the VLF power is to calculate a sum of powers of all frequency domain data corresponding to the heart rate data within a range under 0.04 Hz. The calculation of the ULF power is to calculate a sum of powers of all frequency domain data corresponding to the heart rate data within a range under 0.003 Hz.

The parameters LFnorm, HFnorm and LF/HF may then be calculated based on the parameters LF, HF and TP obtained in the calculation of the frequency power as described above. The calculation of LF/HF is to calculate the ratio of LF to HF. In an illustrative embodiment, the calculation of LFnorm or HFnorm includes dividing the value of LF or HF by the value of the difference between the total power and the VLF, and multiplying the division result by 100, thereby obtaining a normalized LF or HF value.

At the optional operation 1230, a neural network analysis based on the linear HRV parameters may be performed. In illustrative embodiments, the neural network analysis includes at least three linear HRV parameters.

The artificial neural network has a good self-study capability and a capacity of fitting any nonlinear functions. A well-trained neural network has already been self-adjusting during the training procedure and thus once an undetermined parameter value is input into the neural network, it can be determined rapidly whether it belongs to the status of lying or non-lying.

Besides using a well-trained neural network, performing neural network analysis may also include training a neural network. In an illustrative embodiment, the neural network is trained by an Error Back Propagation (EBP) algorithm, so as to get a neural network with the ability to distinguish the physiological characteristics under lying condition from those under non-lying condition.

The error back propagation algorithm is a learning procedure of an artificial neural network, which may include a forward propagation of the signal and a back propagation of the error.

In an illustrative embodiment, the values of five parameters, e.g. LFnorm, HFnorm, LF/HF, TP, and rMSSD, of 16 persons under lying condition and another 16 persons under non-lying condition are provided. Half of those under lying condition are normal persons and the other half are criminal persons. Those values may be used as the input samples for the neural network to make it trained, so that a more accurate five dimension curved surface may be obtained.

Figure 4:
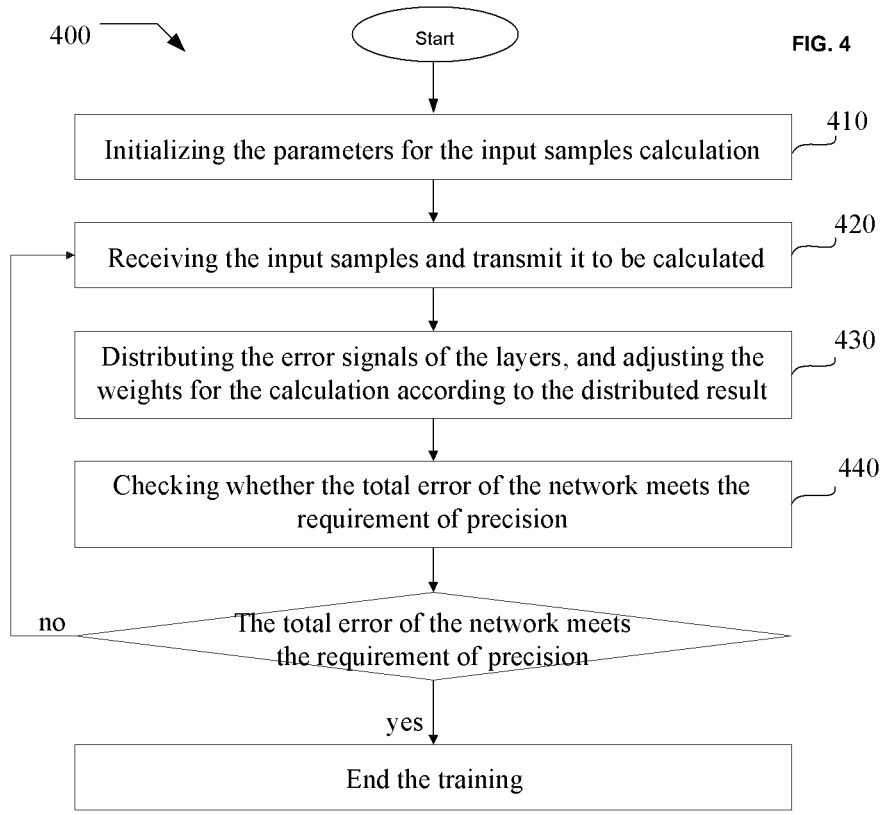
FIG. 4 is a flow chart illustrating an embodiment of error back propagation algorithm.

FIG. 4 illustrates an embodiment of the error back propagation algorithm representing an illustrative embodiment of neural network training using those values as the input samples for the neural network. As shown in FIG. 4, the operational flow 400 includes a parameters initializing operation 410, that includes initializing the parameters for the input samples calculation; an output error obtaining operation 420, that includes obtaining the output error according to the received input samples; a error signals distributing operation 430, that includes distributing the error signals of the layers and adjusting the weights for the calculation according to the distributed result; and a total error checking operation 440, that includes checking the total error of the network.

In the parameters initializing operation 410, the parameters for the input samples calculation are initialized, for example, the weights. The initial values of the weights may be random numbers between 0.2 and 0.4.

In the output error obtaining operation 420, after the input samples are received and transmitted to be calculated, the output error is obtained as the difference between the output value and the expected value.

Supposing the value of non-lying is used as an expected value, the status may be determined as lying when the value output by the output layer is greater than 0.5, and may be determined as non-lying when the value is lower than 0.5. Herein, the value 0.5 may be considered as the maximum error value between the output value and the expected value. That is, when the difference between the output value and the expected value of non-lying does not exceed the maximum error value, it may be considered that the output value is in accord with the expected value of non-lying, and the status is non-lying. Similarly, when the difference between the output value and the expected value of non-lying exceeds the maximum error value, it is considered that the output value is not in accord with the expected value of non-lying, and the status is lying instead of non-lying.

In the error signals distributing operation 430, the error signals of the layers are distributed, and the weights for the calculation are adjusted according to the distributed result.

If the output value from the output layer is not in accord with the expected value, the output error is transmitted backward, so that the error may be distributed over all the calculation, to obtain an error signal from each unit, thereby correcting the weights of the units. Generally a weight may be a random number between −1 to +1. The procedure of adjusting the weights is a procedure of learning and training of the neural network.

In the total error checking operation 440, it is checked whether the total error of the network meets the requirement of precision. If yes, the training is ended; otherwise, the processing returns to the output error obtaining operation 420. For example, supposing 0.5 is a predefined error value, if the total error of the network exceeds 0.5, it may be decided that the output value of the output layer is not in accord with the expected value, and the processing returns to the output error obtaining operation 420.

In illustrative embodiments, when applying a neural network analysis, the parameters used as inputs of the neural network analysis may also be a combination of both linear HRV parameters and nonlinear HRV parameters. The methods to acquire linear HRV parameters and nonlinear HRV parameters can be, but are not limited to, any or all of the methods mentioned above and description thereof is omitted herein.

As shown in FIG. 2, the analysis operation 120 may include optional operations 1240 to 1260 representing an illustrative embodiment of a neural network analysis based on a combination of linear HRV parameters and nonlinear HRV parameters.

At the optional operation 1240, one or more linear HRV parameters may be acquired from the input associated with HRV. At the optional operation 1250, one or more nonlinear HRV parameters may be obtained from the input associated with HRV. At the optional operation 1260, a neural network analysis based on the linear and nonlinear HRV parameters may be performed.

In illustrative embodiments, combinations of linear HRV parameters and nonlinear HRV parameters may include two nonlinear parameters plus one to six linear parameters. Those linear HRV parameters may include, but are not limited to, Total Power (TP), Low Frequency (LF) Power, High Frequency (HF) Power, LFnorm, HFnorm, Low Frequency Power/High Frequency Power (LF/HF), Heart Rate (HR), and Standard Deviation of adjacent R-R Interval (rMSSD), whereas nonlinear HRV parameters may include, but are not limited to, H(m) and PSS. Some illustrative combinations may include LFnorm, LF/HF, HR, H(m) and PSS; LF/HF, HR, rMSSD, H(m) and PSS; LFnorm, LF/HF, TP, H(m) and PSS; TP, LF/HF, HR, H(m) and PSS; and LF/HF, HFnorm, rMSSD, H(m) and PSS. The neural network analysis based on a combination of linear HRV parameters and nonlinear HRV parameters may be performed as described as above.

In certain embodiments, a lie detection method described herein may further comprise outputting one or more of the analysis results or lie detection results in any suitable form, including, without limitation, number values, graphs, and words. In some embodiments, output may be in the form of number values, e.g. of nonlinear HRV parameters such as H(m) and PSS, or neural network analysis results. In some embodiments, output may be in the form of graph, including, without limitation, m-word distribution graph. In some embodiments, output may be in the form of simple words such as "lying" and "non-lying".

In certain embodiments, a lie detection method described herein may further comprise taking a surveillance video and/or tape of the test subject to facilitate interpretation of the analysis results. In this regard, useful information extracted from the surveillance video or tape may include, without limitation, body language, facial expression and change in voice. As with the input associated with HRV, the surveillance video and/or tape may be analyzed on-site, may be stored in a database for later use, or may be transmitted to the analysis site different from where questioning is held by any suitable wireless/wired communication methods, including, without limitation, GSM/GPRS network, Bluetooth, internet and any equivalent means.

In another aspect, the present disclosure provides a method of HRV analysis using strange entropy, comprising taking a time series signal with N elements, u:{u(i):1≤i≤N}, wherein u(i) represents signals carried in the input associated with HRV, and for each u(i), there is a corresponding vector with m elements X(i)=[u(i), u(i+1), . . . , u(i+m−1)]; calculating a base scale BS(i) for each vector X(i); transforming every X(i) to a m-dimensional symbol series $S_i=\{s(i), \ldots s(i+m-1)\}$, s∈A (A=0, 1, 2, 3) based on a scale of a×BS(i); calculating the probability of $S_i$, wherein the probability of each different combination among the entire N−m+1 m-dimensional vectors is $$p(\pi) = \frac{\#\{t \mid (u_i, \ldots, u_{t+m-1}) \text{has type } \pi\}}{N - m + 1},$$

wherein 1≤t≤N−m+1 ; # is the number of states, and each possible combination π for $S_i$ represents a vibration mode for $S_i$; and obtaining one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the following equation:

$$BS(i) = \sqrt{\frac{\sum_{j=1}^{m-1}(u(i+j) - u(i+j-1))^2}{m-1}}.$$

In certain embodiment, said every X(i) is transformed to a m-dimensional symbol series $S_i$ according to the transformation equation:

$$S_{i+k} = \begin{cases} 0: & \bar{u}_i < u_{i+k} \le \bar{u}_i + a \times BS(i) \\ 1: & u_{i+k} > \bar{u}_i + a \times BS(i) \\ 2: & \bar{u}_i - a \times BS(i) < u_{i+k} \le \bar{u}_i \\ 3: & u_{i+k} \le \bar{u}_i - a \times BS(i), \end{cases}$$

wherein i=1, 2, . . . , N−m+1, k=0, 1, . . . m−1; $S_{i+k}$ is the k-th element of $S_i$; $u_{i+k}$ is the k-th element of X(i); $\bar{u}_i$ represents the average value of the m-dimensional vector X(i); and 0, 1, 2, 3 are notation for region partition.

In certain embodiments, said nonlinear HRV parameters include H(m) which is calculated according to the following equation:

$$H(m) = -\Sigma P(\pi)\log_2 P(\pi).$$

In certain embodiments, said nonlinear HRV parameters include PSS which is defined as sum of probabilities of all strange states calculated according to following equation:

$$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

Computer Programs Product, Computer Readable Storage Medium and Systems

In another aspect, the present disclosure provides a computer program product comprising one or more instructions recorded on a machine-readable recording medium for lie detection, wherein the instructions include one or more instructions for receiving an input associated with HRV; and one or more instructions for performing an HRV analysis based on the input associated with HRV to obtain a lie detection result; wherein said HRV analysis includes one or more of nonlinear HRV analysis, or neural network-based linear HRV analysis.

In some embodiments of the computer program product described herein, the instructions may further comprise one or more instructions for outputting one or more of the analysis results or lie detection results.

A person with ordinary skill in the art will appreciate that a computer program product described herein are capable of being distributed in a variety of forms via a signal bearing medium, and that the program product described herein applies regardless of the particular type of signal bearing medium used to actually carry out the distribution. Examples of a signal bearing medium include, but are not limited to, a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

The machine-readable storage media mentioned above include, but not limited to various memories and storage units, a semiconductor device, a disk unit such as an optic disk, a magnetic disk and a magneto-optic disk, and other media applicable to information storage. It is also possible to execute the program on a client computer after computer program codes are downloaded and installed on the computer from a corresponding internet website connected with the computer.

In certain embodiments, said input associated with HRV includes a time series of ECG recordings.

In certain embodiments, the one or more instructions for performing an HRV analysis based on the input associated with HRV include one or more instructions for performing nonlinear HRV analysis based on the input associated with HRV.

In certain embodiments, the one or more instructions for performing non linear HRV analysis based on the input associated with HRV include one or more instructions for performing one or more methods selected from the group consisting of strange entropy (StEn), Chaos, correlation dimension, fractal theory, strange attractors, mode entropy (modEn), multifractal, multiscale multifractal, Lyapunov index, base-scale entropy, and approximate entropy (ApEn).

In some embodiments, the one or more instructions for performing nonlinear HRV analysis based on the input associated with HRV include one or more instructions for performing HRV analysis using strange entropy method.

In an illustrative embodiment, the one or more instructions for performing HRV analysis using strange entropy method include one or more instructions for taking a time series signal with N elements, $u:\{u(i): 1 \leq i \leq N\}$, wherein u(i) represents signals carried in the input associated with HRV, and for each u(i), there is a corresponding vector with m elements $X(i)=$ [u(i), u(i+1), ..., u(i+m-1)]; one or more instructions for calculating a base scale BS(i) for each vector X(i); one or more instructions for transforming every X(i) to a m-dimensional symbol series $S_i=\{s(i), ... s(i+m-1)\}$, $s \in A$ (A=0, 1, 2, 3) based on a scale of a×BS(i); one or more instructions for calculating probability of $S_i$ such that the probability of each different combination among the entire N−m+1 m-dimensional vectors is $$p(\pi) = \frac{\#\{t \mid (u_t, ..., u_{t+m-1}) \text{has type } \pi\}}{N - m + 1},$$

wherein $1 \leq t \leq N-m+1$, # is the number of states, and each possible combination π for $S_i$ represents a vibration mode for $S_i$; and one or more instructions for obtaining one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the equation:

$$BS(i) = \sqrt{\frac{\sum_{j=1}^{m-1} (u(i+j) - u(i+j-1))^2}{m-1}}.$$

In certain embodiment, said every X(i) is transformed to a m-dimensional symbol series $S_i$ according to the transformation equation:

$$S_{i+k} = \begin{cases} 0: & \bar{u}_i < u_{i+k} \leq \bar{u}_i + a \times BS(i) \\ 1: & u_{i+k} > \bar{u}_i + a \times BS(i) \\ 2: & \bar{u}_i - a \times BS(i) < u_{i+k} \leq \bar{u}_i \\ 3: & u_{i+k} \leq \bar{u}_i - a \times BS(i), \end{cases}$$

wherein i=1, 2, ..., N−m+1; k=0, 1, ... m−1; $S_{i+k}$ is the k-th element of $S_i$; $u_{i+k}$ is the k-th element of X(i); $\bar{u}_i$ represents the average value of the m-dimensional vector X(i); and 0, 1, 2, 3 are notation for region partition.

In certain embodiments, said nonlinear HRV parameters include H(m) which is calculated according to the following equation:

$$H(m) = -\Sigma P(\pi) \log_2 P(\pi).$$

In certain embodiments, said nonlinear HRV parameters include PSS which is defined as sum of probabilities of all strange states calculated according to following equation:

$$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

In certain embodiments, the lie detection result is obtained by real-time monitoring using a sliding window. In some embodiments, the size of the sliding window is in the range of 300-500 data points. In some embodiments, a sliding step for the sliding window is between 1 and 50 data points. In some embodiments, said data points represent heart beats.

In certain embodiments, the lie detection result is obtained by comparing the analysis results with normal data.

In certain embodiments, the one or more instructions for performing an HRV analysis based on the input associated with HRV include one or more instructions for performing neural network-based linear HRV analysis based on the input associated with HRV.

In some embodiments, the one or more instructions for performing neural network-based linear HRV analysis based on the input associated with HRV include one or more instructions for acquiring one or more linear HRV parameters from the input associated with HRV; and one or more instructions for performing a neural network analysis based on the linear HRV parameters.

In certain embodiments, the neural network analysis is performed based on at least three linear HRV parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said neural network is trained by an Error Back Propagation algorithm to distinguish lying from non-lying.

In certain embodiments, the one or more instructions for performing HRV analysis include one or more instructions for performing neural network-based linear HRV analysis in combination with nonlinear HRV analysis, wherein the neural network analysis is performed based on a combination of linear HRV parameters and nonlinear HRV parameters.

In some embodiments, the one or more instructions for performing neural network-based linear HRV analysis in combination with nonlinear HRV analysis include one or more instructions for acquiring one or more linear HRV parameters from the input associated with HRV; one or more instructions for obtaining one or more nonlinear HRV parameters from the input associated with HRV; and one or more instructions for performing a neural network analysis based on the linear and nonlinear HRV parameters.

In certain embodiments, said combination of linear HRV parameters and nonlinear HRV parameters includes two nonlinear parameters plus one to six linear parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said nonlinear HRV analysis is performed by using the strange entropy method as described above, and said nonlinear HRV parameters include H(m) and PSS.

In another aspect, the present disclosure provides a computer readable storage medium having a computer program encoded thereon, wherein said computer program when executed by a computer instructs the computer to execute a method of lie detection, which includes receiving an input associated with HRV; and performing an HRV analysis based on the input associated with HRV to obtain a lie detection result; wherein said HRV analysis includes one or more of nonlinear HRV analysis, or neural network-based linear HRV analysis.

In certain embodiments, the computer readable storage medium may be any of a variety of memory storage devices. Examples of memory storage medium include any commonly available random access memory (RAM), magnetic medium such as a resident hard disk or tape, an optical medium such as a read and write compact disc, or other memory storage device.

In certain embodiments, the method of lie detection further includes outputting one or more of the analysis results or lie detection results.

In certain embodiments, said input associated with HRV includes a time series of ECG recordings.

In certain embodiments, said HRV analysis includes nonlinear HRV analysis.

In certain embodiments, said nonlinear HRV analysis is performed by using one or more methods selected from the group consisting of strange entropy (StEn), Chaos, correlation dimension, fractal theory, strange attractors, mode entropy (modEn), multifractal, multiscale multifractal, Lyapunov index, base-scale entropy, and approximate entropy (ApEn).

In certain embodiments, said nonlinear HRV analysis is performed by using strange entropy method.

In certain embodiment, said strange entropy method includes taking a time series signal with N elements, u: $\{u(i): 1 \leq i \leq N\}$, wherein u(i) represents signals carried in the input associated with HRV, and for each u(i), there is a corresponding vector with m elements $X(i)=[u(i), u(i+1), \ldots u(i+m-1)]$; calculating a base scale BS(i) for each vector X(i); transforming every X(i) to a m-dimensional symbol series $S_i=\{s(i), \ldots s(i+m-1)\}$, s∈A (A=0, 1, 2, 3) based on a scale of a×BS(i); calculating probability of $S_i$ such that the probability of each different combination among the entire N−m+1 m-dimensional vectors is $$p(\pi) = \frac{\#\{t \mid (u_i, \ldots, u_{t+m-1}) \text{has type } \pi\}}{N - m + 1},$$

wherein $1 \leq t \leq N-m+1$, # is the number of states, and each possible combination π for $S_i$ represents a vibration mode for $S_i$; and obtaining one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the equation:

$$BS(i) = \sqrt{\frac{\sum_{j=1}^{m-1}(u(i+j)-u(i+j-1))^2}{m-1}}.$$

In certain embodiment, said every X(i) is transformed to a m-dimensional symbol series $S_i$ according to the transformation equation:

$$S_{i+k} = \begin{cases} 0: & \bar{u}_i < u_{i+k} \leq \bar{u}_i + a \times BS(i) \\ 1: & u_{i+k} > \bar{u}_i + a \times BS(i) \\ 2: & \bar{u}_i - a \times BS(i) < u_{i+k} \leq \bar{u}_i \\ 3: & u_{i+k} \leq \bar{u}_i - a \times BS(i), \end{cases}$$

wherein i=1, 2, ..., N−m+1; k=0, 1, ... m−1; $S_{i+k}$ is the k-th element of $S_i$; $u_{i+k}$ is the k-th element of X(i); $\bar{u}_i$ represents the average value of the m-dimensional vector X(i); and 0, 1, 2, 3 are notation for region partition.

In certain embodiments, said nonlinear HRV parameters include H(m) which is calculated according to the following equation $$H(m) = \Sigma P(\pi) \log_2 P(\pi).$$

In certain embodiments, said nonlinear HRV parameters include PSS which is defined as sum of probabilities of all strange states calculated according to following equation $$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

In certain embodiments, the lie detection result is obtained by real-time monitoring using a sliding window. In some embodiments, the size of the sliding window is in the range of 300-500 data points. In some embodiments, a sliding step for the sliding window is between 1 and 50 data points. In some embodiments, said data points represent heart beats.

In certain embodiments, the lie detection result is obtained by comparing the analysis results with normal data.

In certain embodiments, said HRV analysis includes neural network-based linear HRV analysis.

In certain embodiments, said neural network-based linear HRV analysis includes acquiring one or more linear HRV parameters from the input associated with HRV; and performing a neural network analysis based on the linear HRV parameters.

In certain embodiments, the neural network analysis is performed based on at least three linear HRV parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said neural network is trained by an Error Back Propagation algorithm to distinguish lying from non-lying.

In certain embodiments, said HRV analysis includes neural network-based linear HRV analysis in combination with nonlinear HRV analysis, wherein the neural network analysis is performed based on a combination of linear HRV parameters and nonlinear HRV parameters.

In certain embodiments, said combination of linear HRV parameters and nonlinear HRV parameters includes two nonlinear parameters plus one to six linear parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said nonlinear HRV analysis is performed by using the strange entropy method as described above, and said nonlinear HRV parameters include H(m) and PSS.

In another aspect, the present disclosure provides a lie detection system comprising a computing unit configured to receive an input associated with HRV; and perform an HRV analysis based on the input associated with HRV to obtain a lie detection result; wherein said HRV analysis includes one or more of nonlinear HRV analysis, or neural network-based linear HRV analysis.

In certain embodiments, said input associated with HRV includes a time series of ECG recordings.

In certain embodiments, said HRV analysis includes nonlinear HRV analysis.

In certain embodiments, said nonlinear HRV analysis is performed by using one or more methods selected from the group consisting of strange entropy (StEn), Chaos, correlation dimension, fractal theory, strange attractors, mode entropy (modEn), multifractal, multiscale multifractal, Lyapunov index, base-scale entropy, and approximate entropy (ApEn).

In certain embodiments, said nonlinear HRV analysis is performed by using strange entropy method.

In certain embodiments, the lie detection result is obtained by real-time monitoring using a sliding window. In some embodiments, the size of the sliding window is in the range of 300-500 data points. In some embodiments, a sliding step for the sliding window is between 1 and 50 data points. In some embodiments, said data points represent heart beats.

In certain embodiments, the lie detection result is obtained by comparing the analysis results with normal data.

In certain embodiments, said HRV analysis includes neural network-based linear HRV analysis.

In certain embodiments, said neural network-based linear HRV analysis includes acquiring one or more linear HRV parameters from the input associated with HRV; and performing a neural network analysis based on the linear HRV parameters.

In certain embodiments, the neural network analysis is performed based on at least three linear HRV parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said neural network is trained by an Error Back Propagation algorithm to distinguish lying from non-lying.

In certain embodiments, said HRV analysis includes neural network-based linear HRV analysis in combination with nonlinear HRV analysis, and the neural network analysis is performed based on a combination of linear HRV parameters and nonlinear HRV parameters.

In certain embodiments, said combination of linear HRV parameters and nonlinear HRV parameters includes two nonlinear parameters plus one to six linear parameters.

In certain embodiments, said linear HRV parameters include one or more of Total Power, Low Frequency Power, High Frequency Power, LFnorm, HFnorm, Low Frequency Power/High Frequency Power, Heart Rate, and Standard Deviation of adjacent R-R Interval.

In certain embodiments, said nonlinear HRV analysis is performed by using the strange entropy method as described above, and said nonlinear HRV parameters include H(m) and PSS.

In certain embodiments, said lie detection system further comprises an output unit configured to output one or more of the analysis results or lie detection results.

Figure 5:
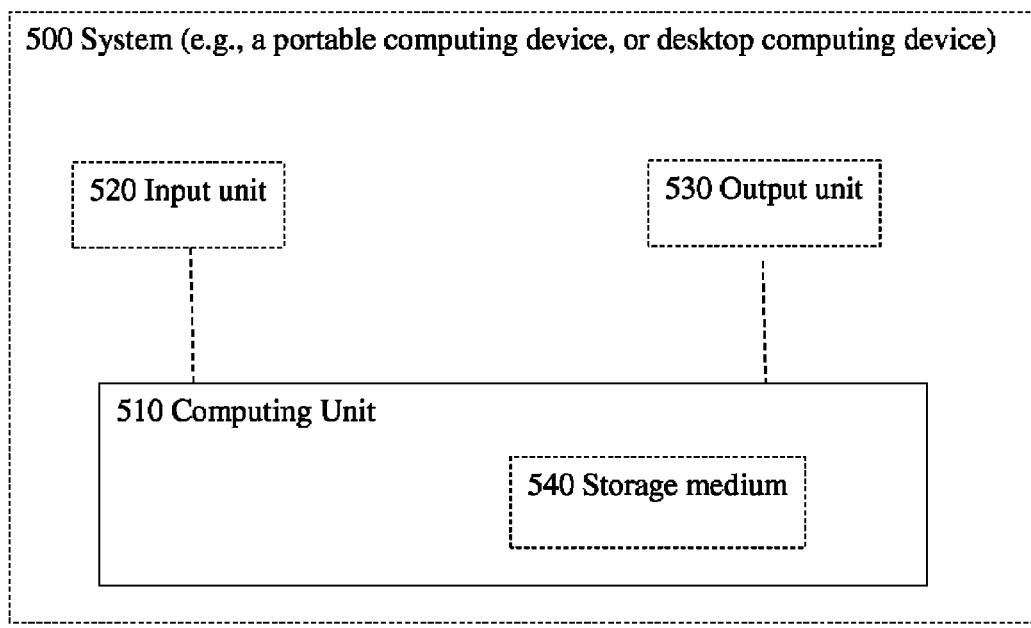
FIG. 5 is a schematic diagram illustrating an embodiment of a lie detection system described herein.

FIG. 5 shows a schematic diagram of an illustrative system 500 in which embodiments may be implemented. The system 500 may include a computing system environment. The system 500 comprises a computing unit 510, and may optionally comprise one or more of an input unit 520, an output unit 530 or a storage medium 540.

In illustrative embodiments, the storage medium 540 is contained in whole or in part within the computing unit 510. In some illustrative embodiments, one or more of the input unit 520, the output unit 530 or the storage medium 540 is in communication with the computing unit 510 by way of an optional coupling. The optional coupling may represent a local, wide area, or peer-to-peer network, or may represent a bus that is internal to the computing unit 510. In an illustrative embodiment, the computing unit 510 may be integrated with one or more of the input unit 520, the output unit 530 or the storage medium 540 into one system unit located at one geographical site. In another illustrative embodiment, one or more of the computing unit 510, the input unit 520, the output unit 530 or the storage medium 540 may be placed into multiple separate system units located at a geographical site or several geographical sites.

In some illustrative embodiments, the computing unit 510 is configured to implement one or more of the techniques, processes, or methods described herein, or other techniques.

In certain embodiments, the computing unit 510 is configured to receive an input associated with HRV; and perform an HRV analysis based on the input associated with HRV to obtain a lie detection result; wherein said HRV analysis includes one or more of nonlinear HRV analysis, or neural network-based linear HRV analysis.

In illustrative embodiments, the computing unit 510 is configured to take a time series signal with N elements, u:{u(i):1≤i≤N}, wherein u(i) represents signals carried in the input associated with HRV, and for each u(i), there is a corresponding vector with m elements X(i)=[u(i), u(i+1), . . . , u(i+m−1)]; calculate a base scale BS(i) for each vector X(i); transform every X(i) to a m-dimensional symbol series $S_i$={s(i), . . . s(i+m−1)}, s∈A (A=0, 1, 2, 3) based on a scale of a×BS(i); calculate probability of $S_i$ such that the probability of each different combination among the entire N−m+1 m-dimensional vectors is $$p(\pi) = \frac{\#\{t \mid (u_i, \ldots, u_{t+m-1}) \text{has type } \pi\}}{N - m + 1},$$

wherein 1≤t≤N−m+1, # is the number of states, and each possible combination π for $S_i$ represents a vibration mode for $S_i$; and obtain one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the equation:

$$BS(i) = \sqrt{\frac{\sum_{j=1}^{m-1}(u(i+j) - u(i+j-1))^2}{m-1}}.$$

In certain embodiment, said every X(i) is transformed to a m-dimensional symbol series $S_i$ according to the transformation equation:

$$S_{i+k} = \begin{cases} 0: & \bar{u}_i < u_{i+k} \leq \bar{u}_i + a \times BS(i) \\ 1: & u_{i+k} > \bar{u}_i + a \times BS(i) \\ 2: & \bar{u}_i - a \times BS(i) < u_{i+k} \leq \bar{u}_i \\ 3: & u_{i+k} \leq \bar{u}_i - a \times BS(i), \end{cases}$$

wherein i=1, 2, . . . , N−m+1; k=0, 1, . . . m−1; $S_{i+k}$ is the k-th element of $S_i$; $u_{i+k}$ is the k-th element of X(i); $\bar{u}_i$ represents the average value of the m-dimensional vector X(i); and 0, 1, 2, 3 are notation for region partition.

In certain embodiments, said nonlinear HRV parameters include H(m) which is calculated according to the following equation $$H(m) = -\Sigma P(\pi) \log_2 P(\pi).$$

In certain embodiments, said nonlinear HRV parameters include PSS which is defined as sum of probabilities of all strange states calculated according to following equation $$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

In some illustrative embodiments, the computing unit 510 may include, but is not limit to, one or more of a desktop computer, a workstation computer, a computing system comprising a cluster of processors, a networked computer, a tablet personal computer, a laptop computer, or a personal digital assistant, or any other suitable computing apparatus. In some embodiments, the computing unit 510 may include one or more of a CPU, a FPGA, a microprocessor, a digital signal processor, an ASIC or any other suitable computing device.

In some illustrative embodiments, the input unit 520 may include, but is not limit to, one of more of a key board, a USB port, a medical testing equipment, or any other suitable input apparatus operable to input data for lie detection and/or HRV analysis. The output unit 530 may include, but is not limit to, one or more of a CRT, a LCD, a printer, an audio speaker or any other suitable output apparatus operable to output one or more of HRV analysis results or lie detection results in a visual format and/or an audio format. The storage medium 540 may include, but is not limited to one or more of a ROM, a RAM, a CD-ROM, a DVD, a tape, a flash memory, or any other suitable medium operable to store data to be processed and/or programs to be executed by the computing unit 510.

In some illustrative embodiments, the medical testing equipment contained in the input unit 510 may include, but is not limit to, a tester operable to provide data that are able to indicate and/or calculate HRV, such as an electrocardiograph, a blood pressure tracking tester, a pulse wave tester and the like.

In another aspect, the present disclosure provides a computer program product comprising one or more instructions recorded on a machine-readable recording medium for performing HRV analysis using strange entropy, wherein the instructions include one or more instructions for taking a time series signal with N elements, $u: \{u(i): 1 \leq i \leq N\}$, wherein $u(i)$ represents signals carried in the input associated with HRV, and for each $u(i)$, there is a corresponding vector with m elements $X(i)=[u(i), u(i+1), \ldots, u(i+m-1)]$; one or more instructions for calculating a base scale $BS(i)$ for each vector $X(i)$; one or more instructions for transforming every $X(i)$ to a m-dimensional symbol series $S_i = \{s(i), \ldots s(i+m-1)\}$, $s \in A$ ($A=0, 1, 2, 3$) based on a scale of $a \times BS(i)$; one or more instructions for calculating probability of $S_i$ such that the probability of each different combination among the entire $N-m+1$ m-dimensional vectors is $$p(\pi) = \frac{\#\{t \mid (u_i, \ldots, u_{t+m-1}) \text{has type } \pi\}}{N-m+1},$$

wherein $1 \leq t \leq N-m+1$, # is the number of states, and each possible combination $\pi$ for $S_i$ represents a vibration mode for $S_i$; and one or more instructions for obtaining one or more of nonlinear HRV parameters or m-word distribution graph according to the probability of $S_i$.

In certain embodiments, $u(i)$ represents R-R interval.

In certain embodiments, $BS(i)$ is defined as square root average of difference between adjacent elements according to the equation:

$$BS(i) = \sqrt{\frac{\sum_{j=1}^{m-1}(u(i+j)-u(i+j-1))^2}{m-1}}.$$

In certain embodiment, said every $X(i)$ is transformed to a m-dimensional symbol series $S_i$ according to the transformation equation:

$$S_{i+k} = \begin{cases} 0: & \bar{u}_i < u_{i+k} \leq \bar{u}_i + a \times BS(i) \\ 1: & u_{i+k} > \bar{u}_i + a \times BS(i) \\ 2: & \bar{u}_i - a \times BS(i) < u_{i+k} \leq \bar{u}_i \\ 3: & u_{i+k} \leq \bar{u}_i - a \times BS(i), \end{cases}$$

wherein $i=1, 2, \ldots, N-m+1$; $k=0, 1, \ldots m-1$; $S_{i+k}$ is the k-th element of $S_i$; $u_{i+k}$ is the k-th element of $X(i)$; $\bar{u}_i$ represents the average value of the m-dimensional vector $X(i)$; and 0, 1, 2, 3 are notation for region partition.

In certain embodiments, said nonlinear HRV parameters include H(m) which is calculated according to the following equation $$H(m) = -\Sigma P(\pi) \log_2 P(\pi).$$

In certain embodiments, said nonlinear HRV parameters include PSS which is defined as sum of probabilities of all strange states calculated according to following equation $$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

A person with ordinary skill in the art will appreciate that a computer program product described herein are capable of being distributed in a variety of forms via a signal bearing medium, and that the program product described herein applies regardless of the particular type of signal bearing medium used to actually carry out the distribution. Examples of a signal bearing medium include, but are not limited to, a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

The machine-readable storage media mentioned above include, but not limited to various memories and storage units, a semiconductor device, a disk unit such as an optic disk, a magnetic disk and a magneto-optic disk, and other media applicable to information storage. It is also possible to execute the program on a client computer after computer program codes are downloaded and installed on the computer from a corresponding internet website connected with the computer.

In another aspect, the present disclosure provides a computer readable storage medium having a computer program encoded thereon, wherein said computer program when executed by a computer instructs the computer to perform HRV analysis using strange entropy, which includes taking a time series signal with N elements, $u: \{u(i): 1 \leq i \leq N\}$, wherein $u(i)$ represents signals carried in the input associated with HRV, and for each $u(i)$, there is a corresponding vector with m elements $X(i)=[u(i), u(i+1), \ldots, u(i+m-1)]$; calculating a base scale $BS(i)$ for each vector $X(i)$; transforming every $X(i)$ to a m-dimensional symbol series $S_i = \{s(i), \ldots s(i+m-1)\}$, $s \in A$ ($A=0, 1, 2, 3$) based on a scale of $a \times BS(i)$; calculating the probability of $S_i$, wherein the probability of each different combination among the entire $N-m+1$ m-dimensional vectors is $$p(\pi) = \frac{\#\{t \mid (u_i, \ldots, u_{t+m-1}) \text{has type } \pi\}}{N-m+1},$$

wherein $1 \leq t \leq N-m+1$; # is the number of states, and each possible combination $\pi$ for $S_i$ represents a vibration mode for $S_i$; and obtaining one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the equation:

$$BS(i) = \sqrt{\frac{\sum_{j=1}^{m-1}(u(i+j)-u(i+j-1))^2}{m-1}}.$$

In certain embodiment, said every X(i) is transformed to a m-dimensional symbol series $S_i$ according to the transformation equation:

$$S_{i+k} = \begin{cases} 0: & \overline{u}_i < u_{i+k} \leq \overline{u}_i + a \times BS(i) \\ 1: & u_{i+k} > \overline{u}_i + a \times BS(i) \\ 2: & \overline{u}_i - a \times BS(i) < u_{i+k} \leq \overline{u}_i \\ 3: & u_{i+k} \leq \overline{u}_i - a \times BS(i), \end{cases}$$

wherein i=1, 2, . . . , N−m+1; k=0, 1, . . . m−1; $S_{i+k}$ is the k-th element of $S_i$; $u_{i+k}$ is the k-th element of X(i); $\overline{u}_i$ represents the average value of the m-dimensional vector X(i); and 0, 1, 2, 3 are notation for region partition.

In certain embodiments, said nonlinear HRV parameters include H(m) which is calculated according to the following equation:

$$H(m) = -\Sigma P(\pi)\log_2 P(\pi).$$

In certain embodiments, said nonlinear HRV parameters include PSS which is defined as sum of probabilities of all strange states calculated according to following equation $$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

In certain embodiments, the computer readable storage medium may be any of a variety of memory storage devices. Examples of memory storage medium include any commonly available random access memory (RAM), magnetic medium such as a resident hard disk or tape, an optical medium such as a read and write compact disc, or other memory storage device.

In another aspect, the present disclosure provides an HRV analysis system, comprising a computing unit configured to take a time series signal with N elements, u:{u(i):1≦i≦N}, wherein u(i) represents signals carried in the input associated with HRV, and for each u(i), there is a corresponding vector with m elements X(i)=[u(i), u(i+1), . . . , u(i+m−1)]; calculate a base scale BS(i) for each vector X(i); transform every X(i) to a m-dimensional symbol series $S_i$={s(i), . . . s(i+m−1)}, s∈A (A=0, 1, 2, 3) based on a scale of a×BS(i); calculate the probability of $S_i$, wherein the probability of each different combination among the entire N−m+1 m-dimensional vectors is $$p(\pi) = \frac{\#\{t|(u_t, \ldots, u_{t+m-1}) \text{ has type } \pi\}}{N-m+1},$$

wherein 1≦t≦N−m+1; # is the number of states, and each possible combination π for $S_i$ represents a vibration mode for $S_i$; and obtain one or more of nonlinear HRV parameters or m-word distribution graph according to the probability of $S_i$.

In certain embodiments, u(i) represents R-R interval.

In certain embodiments, BS(i) is defined as square root average of difference between adjacent elements according to the equation:

$$BS(i) = \sqrt{\frac{\sum_{j=1}^{m-1}(u(i+j)-u(i+j-1))^2}{m-1}}.$$

In certain embodiment, said every X(i) is transformed to a m-dimensional symbol series $S_i$ according to the transformation equation $$S_{i+k} = \begin{cases} 0: & \overline{u}_i < u_{i+k} \leq \overline{u}_i + a \times BS(i) \\ 1: & u_{i+k} > \overline{u}_i + a \times BS(i) \\ 2: & \overline{u}_i - a \times BS(i) < u_{i+k} \leq \overline{u}_i \\ 3: & u_{i+k} \leq \overline{u}_i - a \times BS(i), \end{cases}$$

wherein i=1, 2, . . . , N−m+1; k=0, 1, . . . m−1; $S_{i+k}$ is the k-th element of $S_i$; $u_{i+k}$ is the k-th element of X(i); $\overline{u}_i$ represents the average value of the m-dimensional vector X(i); and 0, 1, 2, 3 are notation for region partition.

In certain embodiments, said nonlinear HRV parameters include H(m) which is calculated according to the following equation $$H(m) = -\Sigma P(\pi)\log_2 P(\pi).$$

In certain embodiments, said nonlinear HRV parameters include PSS which is defined as sum of probabilities of all strange states calculated according to following equation:

$$PSS = \frac{\sum P_s}{\sum_{i=0}^{255} P_i},$$

wherein $P_i$ is probability of combination i, $P_s$ is probability of strange state, and $\Sigma P_s$ is probability sum of all strange states.

In certain embodiments, m is in range of 2-6. In an illustrative embodiment, m is 4.

In certain embodiments, a is in the range of 0.1-2. In certain embodiments, a is in the range of 0.1-0.4. In an illustrative embodiment, a is 0.2.

In certain embodiments, N is larger than $4^m$.

In certain embodiments, the HRV analysis system further comprises one or more of an input unit, an output unit or a storage medium.

There is little distinction left between hardware and software implementations of aspects of systems; the use of hardware or software is generally (but not exclusively, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

EXAMPLES

The following Examples are set forth to aid in the understanding of the present disclosure, and should not be construed to limit in any way the scope of the technology as defined in the claims which follow thereafter.

Example 1

This Example shows an illustrative embodiment of a method of HRV analysis using strange entropy and how it may be used for lie detection. The strange entropy HRV analysis was performed on a young adult, an old adult and a CHF patient, respectively, following the operations described in the Detailed Description above, with symbol number as {0, 1, 2, 3}, dimension m=4 and parameter a=0.2.

Figure 6:
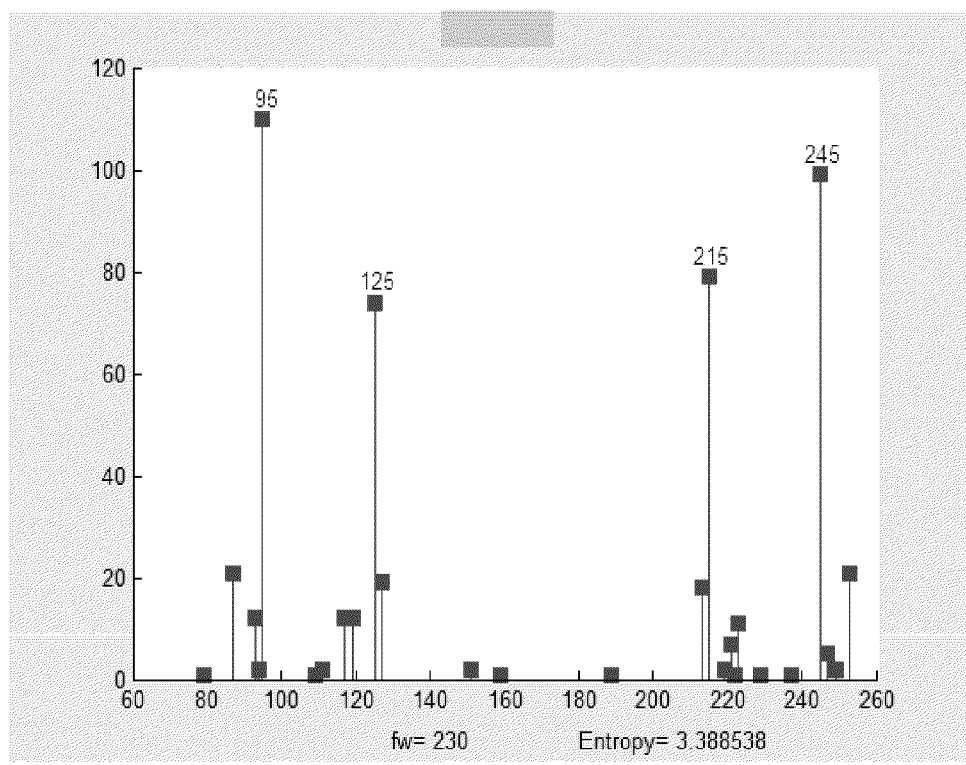
FIG. 6 shows illustrative m-word distribution resulting from nonlinear HRV analysis of a young healthy adult using strange entropy as described herein.

As shown in FIG. 6, a histogram of m-word distribution, largest amplitudes are observed at horizontal value 95, 125, 215, 245, when the HRV analysis using strange entropy was performed on a young adult. Using the language of m-words, those four strange states of the system are respectively 1133, 1331, 3113 and 3311, which are healthy combination states. The same analysis was performed on an old healthy adult, and as shown in FIG. 7, largest amplitudes are also found at horizontal value 95, 125, 215, 245.

Figure 7:
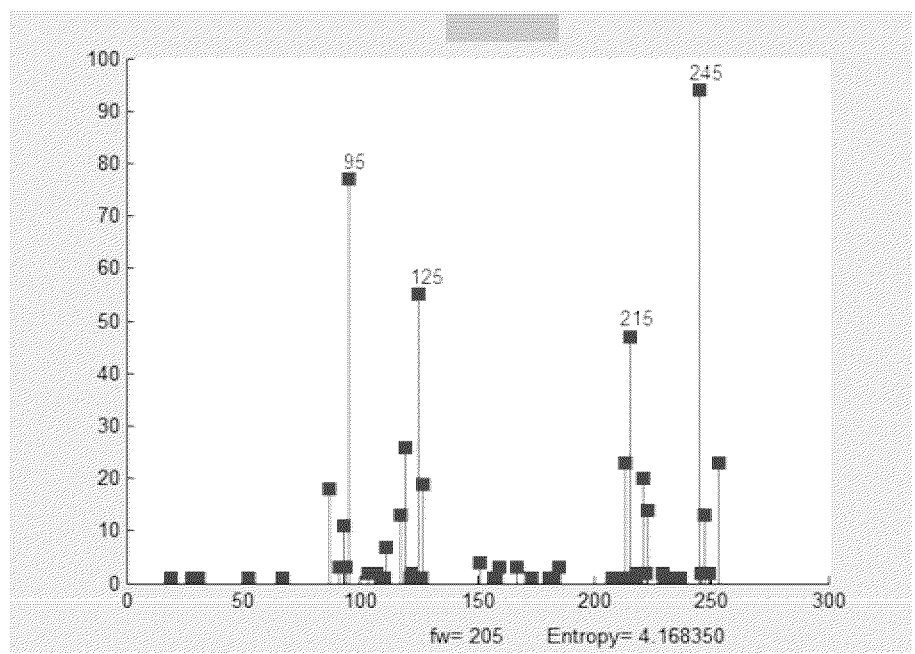
FIG. 7 shows illustrative m-word distribution resulting from nonlinear HRV analysis of an old healthy adult using strange entropy as described herein.

Comparing FIGS. 6 and 7, it is found that the number of the forbidden states in FIG. 6 is larger than that in FIG. 7, showing that physical function of human body degrades with age, since the number of the forbidden states represents health level in a certain extent. However, the four healthy combination states, which have the highest probability, remain the same, i.e. 1133, 1331, 3113 and 3311, respectively, although the probability of each healthy combination state in FIG. 7 is smaller than that of the corresponding healthy combination state in FIG. 6.

Figure 8:
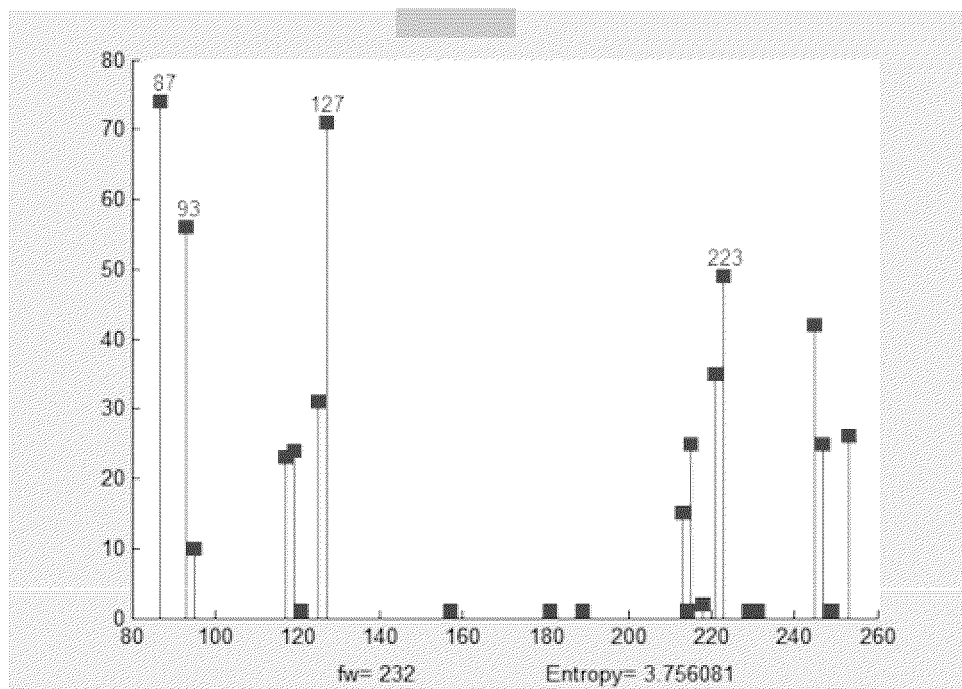
FIG. 8 shows illustrative m-word distribution resulting from nonlinear HRV analysis of a chronic heart failure (CHF) patient using strange entropy as described herein.

In FIG. 8, the test subject was a chronic heart failure (CHF) patient while other test parameters used in the analysis were the same. It is found that largest amplitudes are not at horizontal value 95, 125, 215, 245.

As the comparison between FIGS. 6, 7 and 8 indicates, the four healthy combination states, which are respectively 1133, 1331, 3113 and 3311, have the highest probability and are not relevant to any one or combination of factors such as age, sex, and body shape, whereas persons with heart diseases such as chronic heart failure may present significant variations in the distribution pattern. It can thus be reasonably expected that when a person is under abnormal psychological conditions, such as lying, the distribution pattern will likewise become irregular.

Example 2

Figure 9:
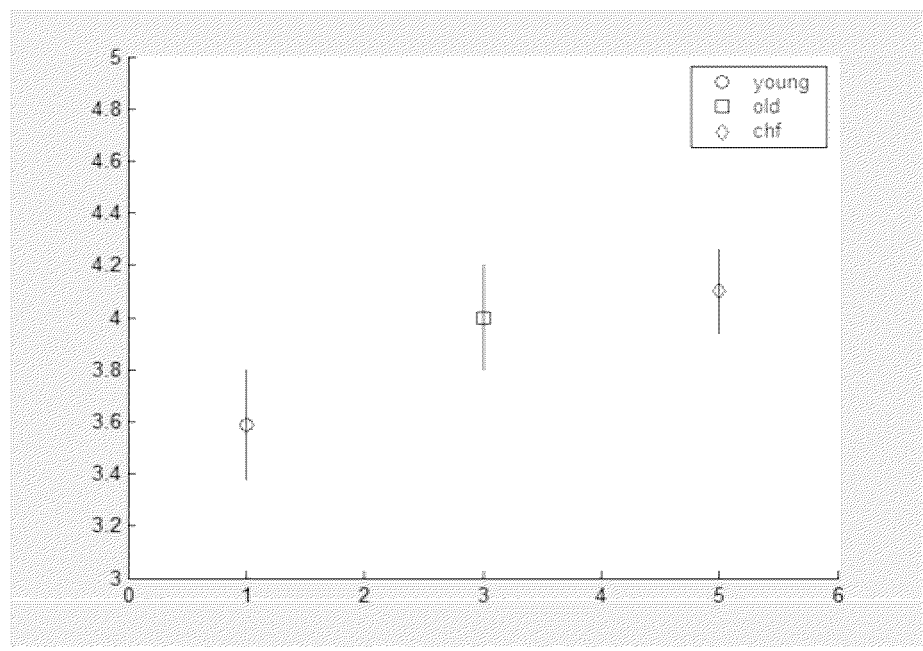
FIG. 9 shows illustrative strange entropy values of young adults, senior adults and CHF patients.
Figure 10:
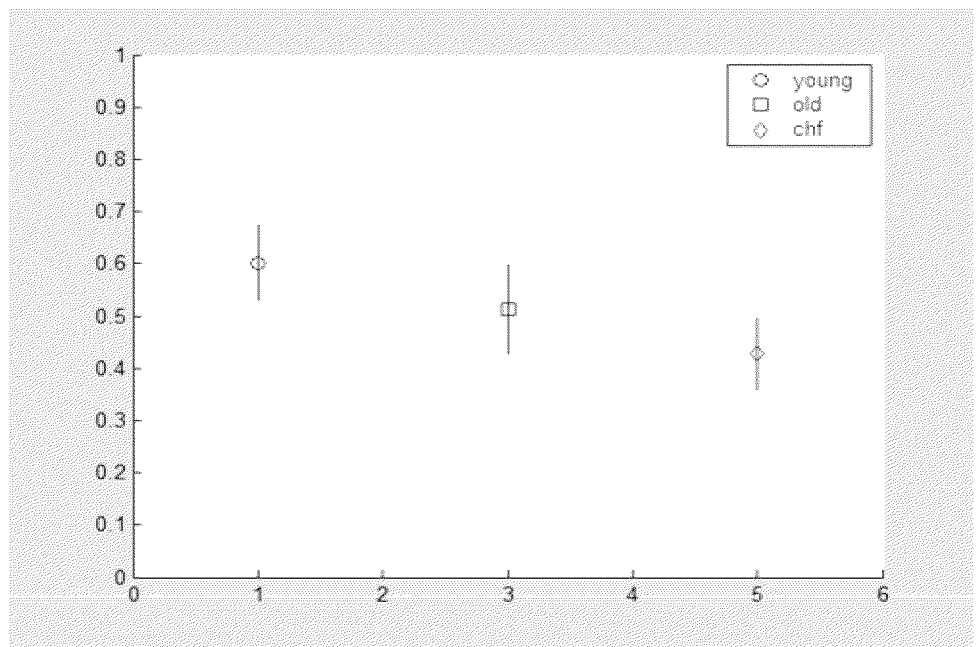
FIG. 10 shows illustrative PSS values of young adults, senior adults and CHF patients.

Using the same methodology as in Example 1, an HRV analysis was performed on a group of young adults, a group of old adults and a group of CHF patients, respectively. FIG. 9 and FIG. 10 show the strange entropy values and the PSS values obtained, respectively (shown as mean±SD).

As can be seen from FIG. 9, the strange entropy value of CHF patients is higher than those of the other two groups of test subjects, the strange entropy value of old adults is higher than that of young adults, and the differences between the strange entropy values of any two groups of test subjects are obvious to be observed and distinguished. As the value of the strange entropy indicates complexity in time series, as well as the self-adjusting ability of parasympathetic system, it increases with disease and aging.

As can be seen from FIG. 10, the total probability PSS of young adults has the highest value and the total probability PSS of CHF patients has the lowest value. The differences between the PSS values of any two groups of test subjects are big enough to be distinguished. The total probability of the strange status PSS increases with decreased sympathetic activity, which occurs when a person is getting older, has degraded physical functions or diseases, or is disturbed by any abnormal psychological conditions, such as lying.

As indicated, the strange entropy value represents complexity in time series, and the PSS value indicates healthy vibration mode of the time series. The more disorder of the healthy vibration mode, the higher complex in time series, and the total probability PSS of the occurrence of strange status decreases, the value of strange entropy increases, accordingly.

Based on the results shown in Example 1 and Example 2, the results of the nonlinear HRV analysis using strange entropy, including m-word distribution, H(m) and PSS values of the test subject, may be compared with normal data, e.g. obtained from a normal person or a group of normal persons, and if there is an irregular or abnormal pattern or a deviation from normal range, it can be determined that the testing subject is lying on the question being asked.

Example 3

This Example shows an illustrative embodiment of a method of lie detection as described herein, using strange entropy nonlinear HRV analysis, by comparing the analysis results obtained from a test subject (a young adult) under anxious condition with those obtained from the same test subject under normal state. The total test lasted about 40 minutes.

Figure 11:
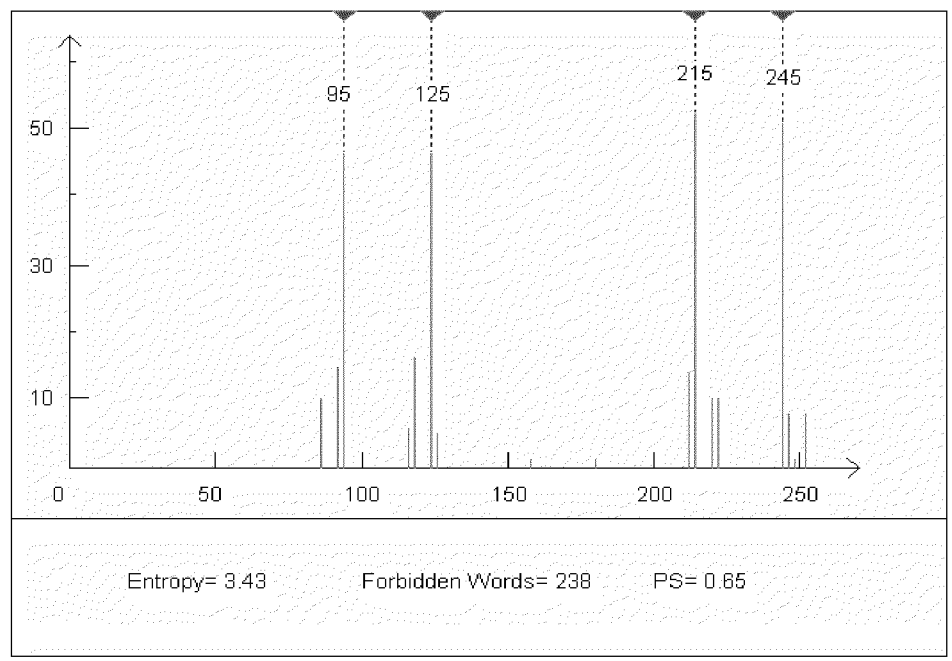
FIG. 11 shows illustrative analysis result of a young adult under normal condition using a strange entropy-based HRV analysis method described herein.
Figure 12:
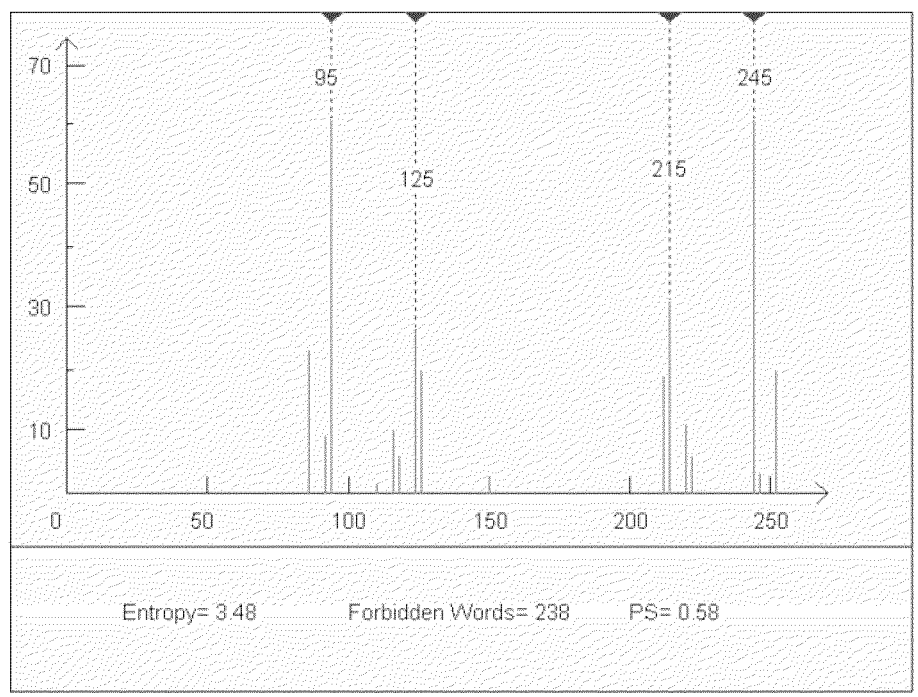
FIG. 12 shows illustrative analysis result of the same young adult under anxious condition using a strange entropy-based HRV analysis method described herein.

FIG. 11 shows a histogram of m-word distribution when the test subject was calm, and FIG. 12 shows a histogram of m-word distribution when the young adult became anxious and uneasy. It is clear that distribution patterns are significantly different between these two psychological states.

In addition, the values of the total probability PSS and strange entropy H(m) of the young adult under these two conditions were calculated, shown as "PS" and "Entropy", respectively, beneath the histograms. When the young adult became anxious, i.e. sympathetic activity increased, the total probability PSS of the occurrence of strange status decreased and the value of strange entropy H(m) increased.

In conclusion, this Example clearly shows that the HRV analysis provided in the present disclosures can sensitively and accurately detect abnormal psychological conditions and thus can be used for lie detection.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or inter-medial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A non-transitory computer-readable storage medium having a computer program encoded thereon, the computer program when executed by a computer instructs the computer to execute a method of lie detection, comprising:
   receiving an input associated with heart rate variability; and
   performing a heart rate variability analysis based on the input associated with heart rate variability to obtain a lie detection result, wherein the heart rate variability analysis includes at least one of nonlinear heart rate variability analysis and neural network-based linear heart rate variability analysis, and wherein the nonlinear heart rate variability analysis is performed by using at least one of strange entropy, Chaos, correlation dimension, fractal theory, strange attractors, mode entropy, multifractal, multiscale multifractal, Lyapunov index, base-scale entropy, and approximate entropy.

2. The non-transitory computer-readable storage medium of claim 1, wherein the input associated with heart rate variability comprises a time series of electrocardiograph recordings.

3. The non-transitory computer-readable storage medium of claim 1, wherein the heart rate variability analysis includes nonlinear heart rate variability analysis.

4. The non-transitory computer-readable storage medium of claim 1, wherein the nonlinear heart rate variability analysis is performed using strange entropy.

5. The non-transitory computer-readable storage medium of claim 1, wherein the nonlinear heart rate variability analysis comprises:

taking a time series with N elements, u:{u(i):1≤i≤N}, wherein u(i) represents signals carried in the input associated with heart rate variability, and for each u(i), there is a corresponding vector with m elements:

$$X(i)=[u(i), u(i+1), \ldots, i-1)];$$

calculating a base scale BS(i) for each vector X(i);
transforming every X(i) to an m-dimensional symbol series $S_i=\{s(i), \ldots -1)\}$, s∈A(A=0,1,2,3) based on a scale of a×BS(i);
calculating the probability of $S_i$, wherein the probability of each different combination among the entire N−m+1 m-dimensional vectors is:

$$p(\pi) = \frac{\#\{t|(u_i, \ldots, u_{t+m-1}) \text{ has type } \pi\}}{N-m+1},$$

wherein 1≤t≤N−m+1; # is the number of states, and each possible combination π for $S_i$ represents a vibration mode for $S_i$;
obtaining nonlinear heart rate variability parameters or m-word distribution graph according to the probability of $S_i$; and
obtaining a nonlinear heart rate variability parameter PSS, which is defined as sum probabilities of all strange states calculated according to the following equation:

$$PSS = \frac{\sum P_s}{\sum_{i=0}^{255} P_i};$$

wherein $P_i$ is probability of combination i, $P_s$ is probability of strange state, and $\Sigma P_s$ is probability sum of all strange states.

6. The non-transitory computer-readable storage medium of claim 1, wherein the lie detection result is obtained by real-time monitoring using a sliding window in a range from about 300 data points to about 500 data points, each of the data points representing a heartbeat.

7. The non-transitory computer-readable storage medium of claim 1, wherein the neural network-based linear heart rate variability analysis comprises at least one of total power, low frequency power, high frequency power, LFnorm, HFnorm, low frequency power / high frequency power, heart rate, and standard deviation of adjacent R-R interval.

8. A non-transitory computer-readable storage medium having a computer program encoded thereon, the computer program when executed by a computer instructs the computer to execute a method of lie detection, comprising:

receiving an input associated with heart rate variability; and
performing a heart rate variability analysis based on the input associated with heart rate variability to obtain a lie detection result, wherein the heart rate variability analysis is performed using strange entropy.

9. The non-transitory computer-readable storage medium of claim 8, wherein the input associated with heart rate variability includes a time series of electrocardiograph recordings.

10. The non-transitory computer-readable storage medium of claim 8, wherein the nonlinear heart rate variability analysis is performed by:

taking a time series signal with N elements, u:{u(i): 1≤i≤N}, wherein u(i) represents signals carried in the input associated with heart rate variability, and for each u(i), there is a corresponding vector with m elements:

$$X(i)=[u(i), u(i+1), \ldots i-1)];$$

calculating a base scale BS(i) for each vector X(i);
transforming every X(i) to an m-dimensional symbol series $S_i=\{s(i), \ldots -1)\}$, s∈A(A =0,1,2,3) based on a scale of a×BS(i);
calculating probability of $S_i$ such that the probability of each different combination among the entire N−m+1 m-dimensional vectors is:

$$p(\pi) = \frac{\#\{t|(u_i, \ldots, u_{t+m-1}) \text{ has type } \pi\}}{N-m+1},$$

wherein 1≤t≤N−m+1,# is the number of states, and each possible combination π for $S_i$ represents a vibration mode for $S_i$; and
obtaining one or more of nonlinear heart rate variability parameters or m-word distribution graph according to the probability of $S_i$.

11. The non-transitory computer-readable storage medium of claim 10, wherein u(i) represents R-R interval.

12. The non-transitory computer-readable storage medium of claim 10, wherein BS(i) is defined as square root average of difference between adjacent elements:

$$BS(i) = \sqrt{\frac{\sum_{j=1}^{m-1}(u(i+j)-u(i+j-1))^2}{m-1}}.$$

13. The non-transitory computer-readable storage medium of claim 10, wherein the every X(i) is transformed to an m-dimensional symbol series $S_i$ according to the transformation equation:

$$S_{i+k} = \begin{cases} 0: & \bar{u}_i < u_{i+k} \leq \bar{u}_i + a \times BS(i) \\ 1: & u_{i+k} > \bar{u}_i + a \times BS(i) \\ 2: & \bar{u}_i - a \times BS(i) < u_{i+k} \leq \bar{u}_i \\ 3: & u_{i+k} \leq \bar{u}_i - a \times BS(i); \end{cases}$$

wherein i=1, 2, . . . , ;$S_{i+k}$ is the k-th element of $S_i$; $u_{i+k}$ is the k-th element of X(i); $\bar{u}_i$ represents the average value of the m-dimensional vector X(i);and 0,1,2, 3 are notations for region partition.

14. The non-transitory computer-readable storage medium of claim 10, wherein the nonlinear heart rate variability parameters include H(m) which is calculated according to the following equation:

$$H(m)=-\Sigma P(\pi)\log_2 P(\pi).$$

15. The non-transitory computer-readable storage medium of claim 10, wherein the nonlinear heart rate variability parameters include PSS which is defined as sum of probabilities of all strange states calculated according to following equation:

$$PSS = \frac{\sum P_s}{\sum_{i=0}^{255} P_i};$$

wherein $P_i$ is probability of combination i, $P_s$ probability of strange state, and $\Sigma P_s$ is probability sum of all strange states.

16. A non-transitory computer-readable storage medium having a computer program encoded thereon, the computer program when executed by a computer instructs the computer to execute a method of lie detection, comprising:
receiving an input associated with heart rate variability; and
performing a nonlinear heart rate variability analysis based on the input associated with heart rate variability to obtain a lie detection result, the nonlinear heart rate variability analysis comprising:
obtaining a nonlinear heart rate variability parameter PSS, which is defined as sum probabilities of all strange states calculated according to the following equation:

$$PSS = \frac{\sum P_s}{\sum_{i=0}^{255} P_i};$$

wherein $P_i$ is probability of combination i, $P_s$ is probability of strange state, and $\Sigma P_s$ is probability sum of all strange states.

17. The non-transitory computer-readable storage medium of claim 16, wherein the nonlinear heart rate variability analysis is performed by using strange entropy method comprising:
taking a time series signal with N elements, $u:\{u(i): 1 \leq i \leq N\}$, wherein $u(i)$ represents signals carried in the input associated with heart rate variability, and for each $u(i)$ there is a corresponding vector with m elements:

$$X(i)=[u(i), u(i+1), \ldots, i-1)];$$

calculating a base scale BS(i) for each vector X(i);
transforming every X(i) to an m-dimensional symbol series $S_i=\{s(i), \ldots -1)\}, s \in A(A=0,1,2,3)$ based on a scale of $a \times BS(i)$;
calculating probability of $S_i$ such that the probability of each different combination among the entire N−m+1 m-dimensional vectors is:

$$p(\pi) = \frac{\#\{t | (u_i, \ldots, u_{t+m-1}) \text{ has type } \pi\}}{N - m + 1},$$

wherein $1 \leq t \leq N-m+1, \#$ is the number of states, and each possible combination $\pi$ for $S_i$ represents a vibration mode for $S_i$; and
obtaining one or more of nonlinear heart rate variability parameters or m-word distribution graphs according to the probability of $S_i$.

* * * * *

UNITED STATES PATENT AND TRADEMARK OFFICE
CERTIFICATE OF CORRECTION

| | |
|---|---|
| PATENT NO. | : 8,543,196 B2 |
| APPLICATION NO. | : 13/407456 |
| DATED | : September 24, 2013 |
| INVENTOR(S) | : Ning |

It is certified that error appears in the above-identified patent and that said Letters Patent is hereby corrected as shown below:

In the Specification

In Column 1, Line 8, delete "2009" and insert -- 2009, --, therefor.

In Column 15, Line 21, delete "$H(m)=\Sigma P(\pi)\log_2 P(\pi)$." and insert -- $H(m) = -\sum P(\pi)\log_2 P(\pi)$. --, therefor.

In Column 19, Line 9, delete "input unit 510" and insert -- input unit 520 --, therefor.

In the Claims

In Column 27, Line 13, in Claim 5, delete "X(i)=[u(i), u(i+1), . . . , i-1)];" and insert -- X(i)=[u(i), u(i+1), . . . , u(i+m-1)]; --, therefor.

In Column 27, Line 16, in Claim 5, delete "$S_i=\{s(i), \ldots -1)\}, s\in A(A=0,1,2,3)$." and insert -- $S_i=\{s(i), \ldots s(i+m-1)\}, s\in A (A=0, 1, 2, 3)$ --, therefor.

In Column 27, Line 44, in Claim 5, delete " $and\Sigma P_s$" and insert -- $and \ \Sigma P_s$ --, therefor.

In Column 28, Line 12, in Claim 10, delete "X(i)=[u(i), u(i+1), . . . i-1)];" and insert -- X(i)=[u(i), u(i+1), . . . , u(i+m-1)]; --, therefor.

In Column 28, Line 15, in Claim 10, delete "$S_i=\{s(i), \ldots -1)\}, s\in A(A =0,1,2,3)based$." and Signed and Sealed this
Eighth Day of April, 2014

Michelle K. Lee
*Deputy Director of the United States Patent and Trademark Office* insert -- $S_i=\{s(i), \ldots s(i+m-1)\}, s \in A\ (A=0, 1, 2, 3)$ based --, therefor.

In Column 28, Line 56, in Claim 13, delete "i=1, 2, . . . , ;$S_{i+k}$" and insert -- i=1, 2, . . . , N-m+1; k=0, 1, . . . m-1; $S_{i+k}$ --, therefor.

In Column 28, Line 58, in Claim 13, delete "X(i);and" and insert -- X(i); and --, therefor.

In Column 30, Line 13, in Claim 17, delete "X(i)=[u(i), u(i+1), . . . , i-1)];" and insert -- X(i)=[u(i), u(i+1), . . . , u(i+m-1)]; --, therefor.

In Column 30, Line 16, in Claim 17, delete "$S_i=\{s(i), \ldots -1)\}, s\epsilon A(A=0,1,2,3)$" and insert -- $S_i=\{s(i), \ldots s(i+m-1)\}, s\epsilon A\ (A=0,1,2,3)$ --, therefor.